(12) United States Patent
Te Raa et al.

(10) Patent No.: US 8,088,344 B2
(45) Date of Patent: Jan. 3, 2012

(54) ROD-SHAPED INSERTS IN REACTOR TUBES

(75) Inventors: Arend Jan Te Raa, The Hague (NL); Mathias Jozef Paul Slapak, Amsterdam (NL); Alouisius Nicolaas Rene Bos, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1202 days.

(21) Appl. No.: 11/525,558

(22) Filed: Sep. 22, 2006

(65) Prior Publication Data

US 2007/0122322 A1    May 31, 2007

Related U.S. Application Data

(62) Division of application No. 10/381,504, filed as application No. PCT/EP01/11138 on Sep. 25, 2001, now Pat. No. 7,132,555.

(30) Foreign Application Priority Data

Sep. 26, 2000    (EP) ..................... 00203362

(51) Int. Cl.
*B01J 8/06* (2006.01)
*F28D 7/00* (2006.01)

(52) U.S. Cl. ........ 422/641; 422/129; 422/201; 422/211; 422/198; 422/600; 422/630; 422/642; 422/643; 422/644; 422/649; 422/650; 422/651; 422/652; 422/659

(58) Field of Classification Search ............... 422/197, 422/129, 201, 198, 211, 600, 630, 641, 642, 422/643, 644, 646, 649–652, 659
See application file for complete search history.

(56) References Cited

U.S. PATENT DOCUMENTS

| 2,856,395 | A | 10/1958 | Richard, Jr. et al. |
|---|---|---|---|
| 3,962,136 | A | 6/1976 | Nielsen et al. |
| 3,970,435 | A | 7/1976 | Schultz et al. |
| 4,010,115 | A | 3/1977 | Nielsen et al. |
| 4,061,659 | A | 12/1977 | Nielsen et al. |
| 4,481,154 | A | 11/1984 | Gough et al. |
| 4,921,681 | A | 5/1990 | Ozero et al. |
| 5,292,904 | A | 3/1994 | Sawada et al. |
| 5,454,429 | A | 10/1995 | Neurauter |
| 2002/0110047 | A1 * | 8/2002 | Bruck et al. .................. 366/340 |

FOREIGN PATENT DOCUMENTS

DE    2413250 A  * 10/1975
(Continued)

OTHER PUBLICATIONS

Machine translation of DE 2413250 A.*

*Primary Examiner* — Walter D Griffin
*Assistant Examiner* — Natasha Young (57) ABSTRACT

A multi-tubular reactor system for catalytically reacting a fluid reactant mixture to form a fluid product comprising a shell and a plurality of reactor tubes housed therein. The reactor system is adapted to allow heat-exchange fluid to flow between the shell and the external surface of the reactor tubes. A reactor tube comprises a reaction zone, and also a heating zone and/or a cooling zone. The reaction zone is positioned downstream of the heating zone. The cooling zone is positioned downstream of the reaction zone. The reactor tube contains a bed of solid particulate catalyst in the reaction zone. The reactor tube additionally contains a heat-exchanging essentially rod-shaped insert having a length of from 1 to 20%, preferably 1 to 5%, of the total length of the reactor tube in the heating zone and/or the cooling zone.

30 Claims, 3 Drawing Sheets

FOREIGN PATENT DOCUMENTS

| | | |
|---|---|---|
| EP | 0 061 154 | 9/1982 |
| EP | 0 266 015 | 5/1988 |
| EP | 0532325 | 9/1992 |
| JP | 2000169463 | 6/2000 |

* cited by examiner

ROD-SHAPED INSERTS IN REACTOR TUBES

This application is a divisional of U.S. patent application Ser. No. 10/381,504, now U.S. Pat. No. 7,132,555, filed Jun. 30, 2003, which is the National Phase of International Application PCT/EP01/11138, filed Sep. 25, 2001, which designated the U.S. and which claims priority to EP 00203362.9, filed Sep. 26, 2000, with the European Patent Office. The entire disclosures of these applications are hereby incorporated by reference.

FIELD OF THE INVENTION

The present invention relates to a process and associated apparatus and systems for catalytically reacting a fluid reactant mixture in a multi-tubular reactor system.

BACKGROUND OF THE INVENTION

Catalytically enhanced reaction processes are used in the synthesis of hydrocarbons and their oxygenated derivatives by the catalytic hydrogenation of carbon monoxide (the Fischer-Tropsch process) and in the epoxidation of alkenes. Such reactions are typically highly exothermic. They are generally performed in a vertical shell-and-tube exchanger type reactor comprising a multitude of reaction tubes, each containing a solid particulate catalyst and surrounded by a heat-exchange fluid.

Typically, a production of ethylene oxide can be performed by the catalytic oxidation in the vapour phase of ethylene with a molecular oxygen-containing gas. Shell-and-tube reactors used for ethylene oxidation contain several thousands of reaction tubes, each 6-15 m long and each having an inside diameter of between 20-50 mm. The ethylene oxidation solid particulate catalysts are generally based on silver supported on an inert carrier material, to which promoters and co-promoters may be added. Supported ethylene oxidation catalysts comprising silver and one or more of the alkali metals K, Rb and Cs are disclosed in U.S. Pat. Nos. 3,962,136 and 4,010,115. Supported ethylene oxidation catalysts comprising silver, rhenium, at least one further metal and optionally a rhenium co-promoter are disclosed in EP-B 0 266 015. A heat-exchange fluid can be a hydrocarbon or a mixture of hydrocarbons, or it can be water.

The reaction of ethylene oxidation is conducted at a temperature which is broadly in the range of from 150 to 350° C. Depending on the reactor design, the catalyst composition, the feed composition and the further reaction conditions a narrow reaction temperature range has to be maintained within any given reactor. The operation involves the pre-heating of the incoming feed gases in the upstream portion of the reaction tubes to the required reaction temperature, removing excess heat during the reaction, and cooling down the effluent of the reaction.

For greater efficiency of the pre-reaction heating and post-reaction cooling, the upstream and/or downstream portions of the ethylene oxidation reactor tubes are traditionally packed with particulate material (also termed packing). Such particulate material may or may not be the same as the particulate catalyst used. In the former case, expensive catalyst is being used as an inert. In U.S. Pat. No. 5,292,904 the use is disclosed of inert particles as packing material in an upstream preheating zone and in a downstream cooling zone of multi-tubular reactors for the production of ethylene oxide. U.S. Pat. No. 4,061,659 is directed to a process for the production of ethylene oxide in a multi-tubular reactor, whereby the downstream portion of the reactor tubes is filled with an inert refractory particulate material having a surface area of 0.1 $m^2/g$ or less.

Japanese patent publication JP2000-169463-A envisages the use of stainless steel packing as inert material, the main advantage being that stainless steel is less prone to by-product formation. It should be noted that it is well known, see e.g. Wakao & Kaguei, Heat transfer in packed beds; Gordon & Breach, 1982), that for tubes filled with particulates, the thermal conductivity of the packing material has little influence on the heat transfer under turbulent flow conditions. Therefore, there would be no significant improvement of heat transfer expected when applying (stainless) steel as compared to low conductivity materials such as silica.

When inert particles are used in the upstream and/or downstream portion of the reactor tubes, they have the advantages of being less expensive and having a longer useful life than catalyst particles. On the other hand, their separation from exhausted catalyst introduces a complication.

There exists therefore a need for the use of a different kind of inserts in the upstream and/or downstream portion of the reactor tubes. These inserts should be at least as efficient as the known particulate filling materials in promoting the pre-heating and/or post-cooling of the feed gases. In particular, their heat transfer coefficient should be high and the gas pressure drop caused by them should be low. Moreover, they should be inexpensive and easily separable from the catalyst particles.

The use of coherent inserts of varying and more or less complicated shapes is known in the art of heat exchange, but not in chemical reactors. They are generally designed to cause maximal turbulence of the fluid—mostly liquid—flowing through. Indeed, they are frequently called turbulators or turbulence inserts.

An example of an insert having a complicated shape is to be found in EP-B 0 061 154, wherein an insert for placement in a vessel is disclosed, comprising an elongated core having a plurality of loops disposed longitudinally therealong and angularly thereabout wherein a portion of each loop lies in close proximity to a conceptual enveloping surface, so that laterally rectilinear lines (L) extending from the core to the midpoint of said portion are disposed at different longitudinal positions along the core, characterised in that each line (L) of each loop lies at an acute angle to the core. Preferably, the core comprises two elongated elements twisted together, a part of each of said loops being held between the twisted together elements.

In U.S. Pat. No. 5,454,429 a forced-flow heat exchanger is disclosed, comprising a housing as part of an outer thermal cycle and at least one tube attached in parallel to the longitudinal housing axis as part of an inner thermal cycle, wherein each of said tubes comprises a loosely inserted flexible rod which is freely movable and rotable in the axis and radial tube directions. The flexibility of the rods and their being freely movable are stated to be very essential features, since the resulting vibrations promote a turbulent flow inside the tubes. The rods according to this disclosure are relatively thin, the preferred ratio between the inside tube diameter and the rod diameter being from 1.4 to 2.5. The rods occupy the entire length of the tubes.

This and the further art searched contains no reference to the use of any type of coherent (as opposed to particulate) insert for promoting the pre-heating of reactants in a chemical multi-tubular reactor, in particular when the reactants are gaseous and more in particular when they comprise a carbon monoxide/hydrogen or an ethylene/oxygen reaction mixture.

SUMMARY OF THE INVENTION

It has now been found that for the intended use of promoting the pre-heating and/or post-cooling of the reaction gases in the upstream and/or downstream portion of multi-tubular reactors which further contain solid catalyst particles, an essentially rod-shaped insert made of an inert material and having a length of from 1 to 20%, preferably 1 to 5%, of that of the reactor tube is at least as effective as is a multitude of packing particles occupying the same length, while having the additional advantages of being inexpensive and easy to insert and to remove. Where greater heating/cooling efficiency is provided by the use of such inserts to promote pre-heating and/or post-cooling, this has the further advantage that it enables, if so desired, the shortening of the heating and/or cooling zone in a catalytic reactor tube.

The present invention therefore involves a process for catalytically reacting a fluid reactant mixture in a multi-tubular reactor system to form a fluid product, whereby the reactant mixture is led through at least one reactor tube containing a fixed bed of solid particulate catalyst and surrounded by a heat-exchange fluid, and whereby an upstream portion of the reactor tube is dedicated to pre-heating the reactant mixture and/or a downstream portion of the reactor tube is dedicated to post-cooling the product, characterised in that said upstream portion and/or downstream portion of each reactor tube contain a heat-exchanging essentially rod-shaped insert, the insert having a length of from 1 to 20%, preferably 1 to 5%, of the total length of the reactor tube.

In particular, the reactant mixture comprises carbon monoxide and hydrogen and the product comprises a hydrocarbon and/or an oxygenate thereof, or the reactant mixture comprises an alkylene and oxygen and the product comprises an alkylene oxide. More in particular, the reactant mixture comprises ethylene and oxygen and the product comprises ethylene oxide.

BRIEF DESCRIPTION OF THE DRAWINGS

A more particular description of the invention, briefly summarized above, may be had by reference to the embodiments thereof which are illustrated in the appended drawings and described herein. It is to be noted, however, that the appended drawings illustrate only some embodiments of the invention and are therefore not to be considered limiting of its scope for the invention may admit to other equally effective embodiments.

DETAILED DESCRIPTION OF THE INVENTION

Figure 1:
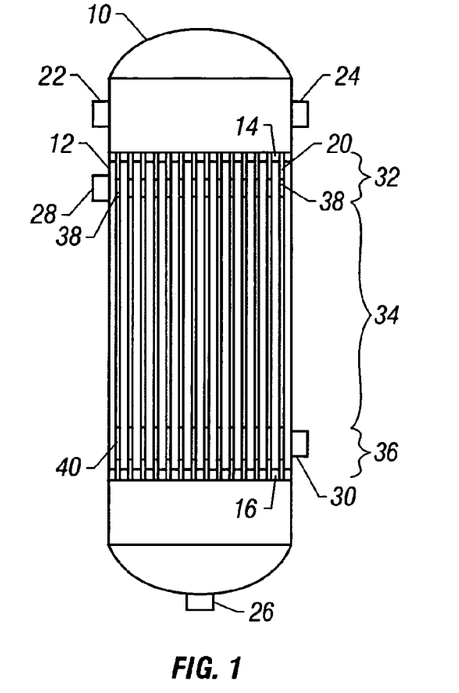
FIG. 1 is an exemplary cross sectional schematic view of a reactor having inserts disposed therein.

FIG. 1 is an exemplary cross sectional schematic view of a reactor having inserts disposed therein. A reactor 10 comprises a shell 12 housing one or more reactor tubes 20. A first tube plate 14 is disposed concentrically within the shell and is coupled to the tubes 20 to provide lateral support for the tubes. Similarly, a second tube plate 16 is coupled to another portion of the tubes 20 to provide lateral support therefor. One or more inlets, such as inlets 22, 24, are formed in the reactor 10 to allow reactants to enter the reactor. One or more outlets, such as outlet 26, are formed in the reactor 10 to allow a resulting product to exit the reactor. Temperature control inlet 28 and outlet 30 allow cooling/heating fluid to enter and exit, the reactor 10, respectively.

The reactor 10 can be divided into a heating zone 32, a reaction zone 34, and a cooling zone 36. The order, size, and existence of the zones and inlets/outlets can vary depending on whether the reaction is endothermic or exothermic, the speed of the reaction, flow rate, and other factors. A catalyst is generally disposed within the reactor tubes 20 in the reaction zone 34.

One or more, and generally all, of the reactor tubes 20 have one or more inserts 38 disposed therein. While it is feasible for a mixture of inserts to be used for a single reactor, for economical and practical reasons, it may be desired that all inserts will be the same in a single reactor.

In some embodiments, such as shown in FIG. 1, one set of inserts 38 can be disposed in an upstream portion of the reactor tubes 20 and another set of inserts 40 can be disposed in a downstream portion of the reactor tubes.

Further, it is possible for certain tubular reactors, such as those utilised in the catalytic conversion of ethylene and oxygen to ethylene oxide, that an efficient usage of the inserts proposed by the present invention is to have one size of insert in the upstream portion of a reactor tube 20 and a different size of insert in the downstream portion. In such situations, the upstream insert 38 would suitably be of shorter length than the downstream insert 40, and very suitably it would be approximately half the length of the downstream insert. For example, the upstream insert 38 may have a length of from 1 to 10%, or from 1 to 5%, of the total length of the reactor tube, and the downstream insert 40 may have a length of from 2 to 20%, or from 2 to 10%.

An inside heat transfer coefficient of the inserts according to the present invention is suitably from 800 to 4000 $Wm^{-2}K^{-}$ (Watt per $m^2$ per degree Kelvin), based on inner tube surface area, when measured at Reynolds numbers in the range of from 10,000 to 50,000, based on void tube dimensions and superficial velocity.

The pressure drop along a portion of the reactor tube 20 occupied by the inserts 38, 40 according to the present invention is suitably from 50 to 20,000 Pa per metre, also when measured at Reynolds numbers in the range of from 10,000 to 50,000, based on void tube dimensions and superficial velocity.

Figure 2:
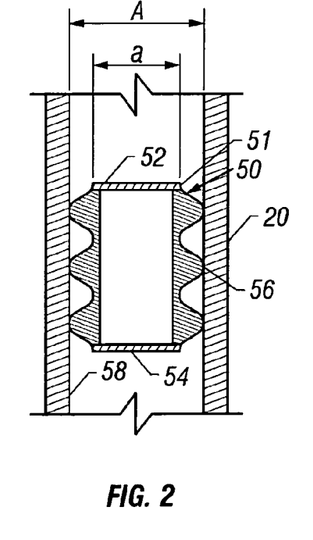
FIG. 2 is a longitudinal cross sectional schematic view of one exemplary insert.

FIG. 2 is a longitudinal cross sectional schematic view of one exemplary insert. An insert 50 can be disposed into a reaction tube 20. The insert according to the present invention can have various shapes. The insert 50 shown in FIG. 2 can have a core 51 with a substantially cylindrical shape. The insert 50 is preferably hollow, and closed on at least one end 52, more preferably at both ends, 52, 54.

A cross-sectional external dimension "a" of the core 51 defines a cross-sectional external surface area of the core 51. A cross-sectional dimension "A" of an inside surface 58 of the reaction tube defines a cross-sectional internal surface area of the reactor tube portion in which the insert 50 is disposed. Generally, the cross-sectional external surface area of the core 51 can be from about 20 to 90% of the cross-sectional internal surface area of the reactor tube 20.

The insert 50 can comprise surface protrusions 56, such as rings, bars, helices, other shaped protrusions, or a combination thereof, extending circumferentially or longitudinally along the length of the insert. The protrusions generally contact the inside surface 58 of the reactor tube 20 and secure the insert in position inside the reactor tube.

Figure 3:
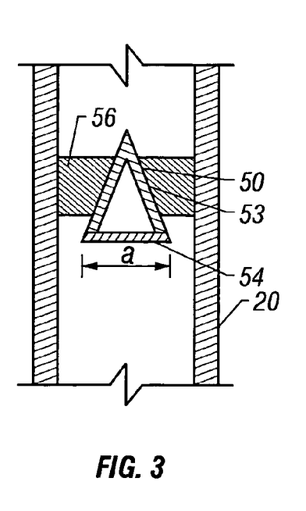
FIG. 3 is a longitudinal cross sectional schematic view of another embodiment of an insert.

FIG. 3 is a longitudinal cross sectional schematic view of another embodiment of an insert. Similar to FIG. 2, an insert 50 with surface protrusions 56 can be disposed within a reactor tube 20. The insert 50 can have a conical shape. The cone can also be preferably hollow, and closed at one end 54. The insert 50 can have an upstream taper 53. The insert can also have a downstream taper (not shown).

It is to be understood that the insert shape can vary and can be any geometric shape as is appropriate to the purposes of the invention.

Figure 4:
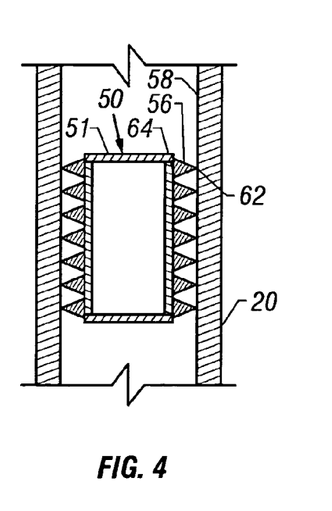
FIG. 4 is a longitudinal cross sectional schematic view of another embodiment of the insert.

FIG. 4 is a longitudinal cross sectional schematic view of another embodiment of the insert. An insert 50 is shown disposed in a reactor tube 20 on an inside surface 58 of the tube. The insert 50 can have an elongated core 51. As one example, the core 51 can have a cross-sectional external surface area of from about 20 to 90%, for example about 20 to 80% of the cross-sectional internal surface area of the reactor tube.

The core 51 can comprise one or more surface protrusions 56, such as wire mesh, brush bristles, longitudinally positioned smooth or corrugated plates, fins or wings of any shape and direction, or a combination thereof. Generally, at least some of the protrusions contact the inside surface 58 of the reactor tube 20 and secure the insert in position inside the reactor tube. In some embodiments, the surface areas and/or thicknesses of the individual protrusions 56 can increase from an outer periphery 62 of the protrusion 56 towards a base 64 of the protrusion 56 and the outer circumference of the core 51.

Figure 5:
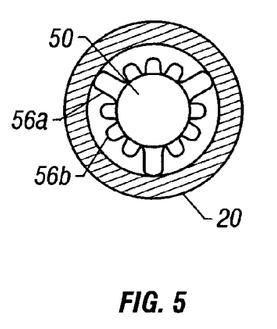
FIG. 5 is an exemplary end view of an insert disposed in a reactor tube.

FIG. 5 is an exemplary end view of an insert 56 disposed in a reactor tube 20. It will be appreciated that in at least some embodiments, it is not necessary for each and every protrusion to contact the reactor tube 20, but merely that sufficient contact from the one or more protrusions secure the inset in position during use. For example, extended protrusions 56a can contact the reactor tube 20 and other protrusions 56b may not contact the reactor tube.

Figure 6:
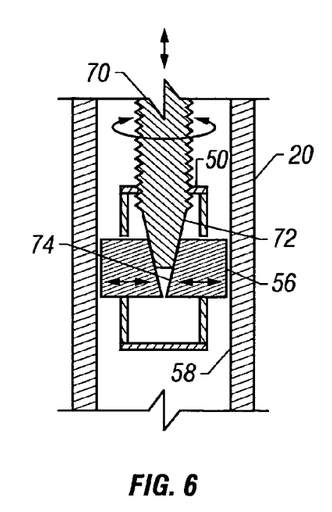
FIG. 6 is a longitudinal cross sectional schematic view of one or more expandable protrusions of an insert in a retracted position.
Figure 7:
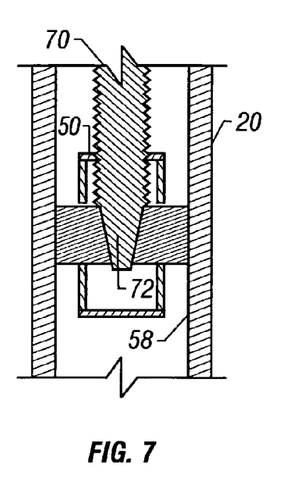
FIG. 7 is a longitudinal cross sectional schematic view of the expandable protrusions in an expanded position.
Figure 8:
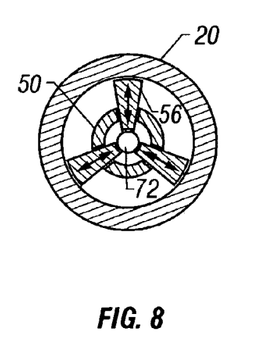
FIG. 8 is a cross sectional schematic end view of the insert and reactor tube of FIG. 6.

FIGS. 6-8 are cross sectional schematic views of another embodiment of the insert. FIG. 6 is a longitudinal cross sectional schematic view of one or more expandable protrusions of an insert in a retracted position. FIG. 7 is a longitudinal cross sectional schematic view of the expandable protrusions in an expanded position. FIG. 8 is a cross sectional schematic end view of the insert and reactor tube of FIG. 6. FIGS. 6-8 will described concurrently with each other.

To place an insert 50 into a reactor tube 20, it can be useful that the associated protrusions 56 do not contact the inside surface 58 of the reactor tube until after the insert is positioned in the tube. To assist contact of one or more protrusions 56, shown in FIGS. 1-5, against the inside surface 58 of a reactor tube 20 once in place, a very useful embodiment is one wherein the insert 50 can be adjusted once in position to force the protrusions against or towards the inside surface of the reactor tube. A number of methods and systems can be used for expanding the protrusions can be used, including, but not limited to threaded engagements, slip engagements, cams, beveled surfaces, gas and hydraulic activation, and other methods, as would be apparent to those with ordinary skill in the art, given the understanding provided by the description of the invention contained herein.

For example and without limitation, the insert 50 can include a translatable member 70 that can have a twist point 72 at one end. The twist point 72 can engage a beveled surface 74 on the protrusion 56. The twist point 72 can be turned, once the insert 50 is in position, such that the projections 56 are expanded within the reactor tube 20 and the protrusions contact the inside surface 58 or are brought into closer proximity to the inner surface of the reactor tube. Although not shown, it is to be understood that the insert itself or its core can also be expanded in addition to or in lieu of the protrusion to achieve a similar result, that is, expansion of at least some member of the insert toward the reactor tube 20.

Figure 9:
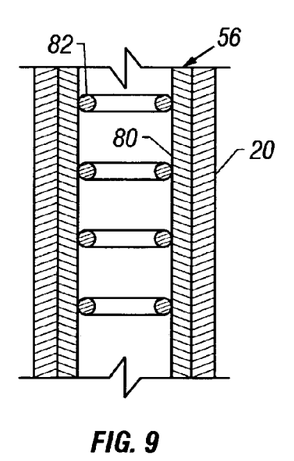
FIG. 9 is a longitudinal cross sectional schematic view of another embodiment of the insert.
Figure 10:
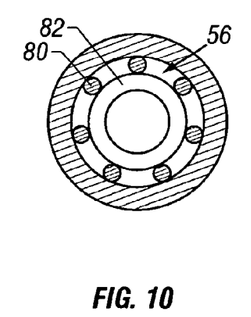
FIG. 10 is a cross sectional schematic end view of the insert.

FIG. 9 is a longitudinal cross sectional schematic view of another embodiment of the insert. FIG. 10 is a cross sectional schematic end view of the insert and reactor tube of FIG. 9 and will be described concurrently with FIG. 9.

An insert 56 can be disposed in a reactor tube 20. The insert 56 can have a rod-shaped, but core-less, form, such as a quantity of wire mesh. The insert 56 can be sized to fit with its periphery adjacent to the tube's inside surface and so fit snugly into the reactor tube. For example, the wire mesh can include longitudinal members 56 and lateral members 82. The insert 56 can be formed into an appropriate shape and size to fit within the reactor tube 20.

Regardless of the particular shape and configuration, preferably each insert is made of a metal or an alloy which is sufficiently conductive to heat and resistant to corrosion under the reaction conditions, such as carbon steel or stainless steel. The metal/alloy of choice may vary depending upon the reaction carried out in the tubular reactor.

Exemplary Process for Use With Insert

Exemplary to the operation of a process according to the present invention is the epoxidation of ethylene. The processes for the catalytic production of ethylene oxide in the vapour phase from ethylene and molecular oxygen are broadly divided according to the source of oxygen used, into those using pure oxygen and those using air—but the differences with regard to heat transfer requirements are not fundamental and the present invention can be applied in both cases.

Whether pure oxygen or air is used in the oxidation of ethylene, the reaction gas mixture in both cases comprises, besides ethylene and oxygen, an excess of diluents such as carbon dioxide, nitrogen, argon, methane and ethane, and a small quantity of a halide reaction moderator such as ethyl chloride, vinyl chloride or dichloroethane. For example, the reaction gas may contain by volume 1-40% of ethylene, 3-12% of oxygen, 0-3% of ethane, 0.3-50 ppm chlorohydrocarbon moderator and balance argon and/or methane.

The inlet reaction gas pressure is in the range of from atmospheric to 4000 kPa, preferably from 1000 to 3000 kPa. It is important that the insert according to the invention does not cause a substantial pressure drop over the length of reactor tube which they occupy. Preferably the pressure drop is less than about 2% of the inlet pressure.

The reaction (catalyst) temperature is in the range of from 150 to 350° C., preferably from 220 to 300° C. The Volume Hourly Space Velocity (VHSV) of the reaction gas mixture is in the range of from 1000 to 10000 h$^{-1}$ (m$^3$ per m$^3$·h of packed catalyst) and preferably from 2000 to 8000 h$^{-1}$ (m$^3$ per m$^3$·h of packed catalyst), measured at standard temperature and pressure conditions. VHSV is typically expressed in units of hour$^{-1}$, cubic meter per cubic meter-hour, cubic meter of gas per cubic meter of reactor volume (eg packed catalyst volume)-hour, or other like volume per volume-time units. The O$_2$ conversion level is 10-60% and the EO production (work rate) 30-400 kg/m$^3$ catalyst/hr.

When a hydrocarbon is used as the heat-exchange fluid surrounding the reactor tubes, its pressure is generally between 100 and 1500 kPa, preferably between 200 and 800 kPa, more preferably between 200 and 600 kPa. When the heat-exchange fluid is water, its pressure is between 1500 and 8000 kPa. The temperature of the heat-exchange fluid on leaving the reactor is generally between 200 and 350° C., preferably between 220 and 300° C.

The following non-limiting examples illustrate embodiments of the invention.

In Examples 1 and 2, two illustrative embodiments of inserts according to the present invention are given.

In Examples 3 to 5, the theoretical/calculated performance, in terms of effect on heat transfer, pressure drop and turbulence respectively, of the (gaseous) fluid flowing through a tubular reactor, was determined on the basis of:
 inserts according to Examples 1 and 2 respectively, made of carbon steel having a specific conductivity of 45 Wm$^{-1}$K$^{-1}$,
 a 35 cm bed of particulate catalyst material, i.e alpha silver-impregnated alpha alumina rings (outer diameter 8.40 mm, inner diameter 2.97 mm, height 8.55 mm), and
 a void reactor tube.

Example 1

Insert

Figure 11:
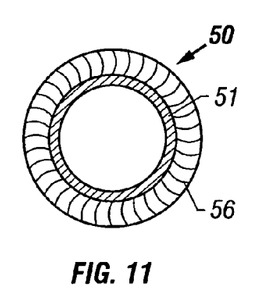
FIG. 11 is a schematic cross sectional end view of an insert.

FIG. 11 is a schematic cross sectional end view of an insert. The insert 50 included a construction of 32 bent fins as protrusions 56, welded individually around a central core 51 or annulus, which is a hollow cylinder, closed at one end or both ends and having an outside diameter of 25 mm. The thickness of the fin material is 1 mm and the total height of each bent fin is 8.1 mm. The outer diameter of the construction is 38.5 mm and its length 35 cm.

Example 2

Insert

Figure 12:
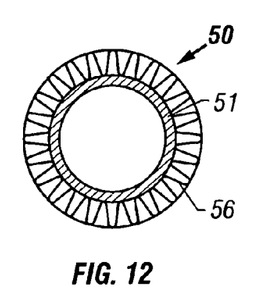
FIG. 12 is a schematic cross sectional end view of an insert.

FIG. 12 is a schematic cross sectional end view of an insert. The insert 50 included a construction of a 1 mm stainless steel plate formed into protrusions 56, that is, the plate was corrugated with corrugation length of 5 mm and a corrugation height of 6.75 mm, bent around the core 51, similar to such in Example 1. The outer diameter of the construction is 38.5 mm and its length 35 cm.

Example 3

Heat Transfer

A reactor tube is used, having an internal diameter of 38.5 mm and a length of about 35 cm, that being about 3% of the total length of a typical commercial reactor tube. The reactor tube is charged with the inserts of Examples 1 and 2 (each also having a length of 3% of the total length of a typical commercial reactor tube), with the ring-formed particles, or left void, and is heated to 250° C. A gaseous mixture of methane (50%), ethylene (40%) and oxygen (10%) enters the reactor tube at a superficial velocity of 1 ms$^{-1}$, 2000 kPa and 150° C.

The heat transfer inside the tube charged with the inserts of Examples 1 and 2 and the heat transfer inside the void tube is determined according to the heat transfer relations of V. Gnielinski, "Chem.-Ing.-Techn.", 61, (1989), 160/61, assuming a state steady heat transfer, a constant heat transfer coefficient at the surface of the insert, a homogeneous material of the insert, no heat production, no resistance in heat conduction between the tube wall and the insert, and no radial temperature gradients in the fluid. The heat transfer inside the tube charged with ring-shaped particulates ("packed bed"), is determined according to P. C. Borman, et al., Chem. Engng. Commun., vol 114, pp. 17 to 47, under the same set of assumptions.

Figure 13:
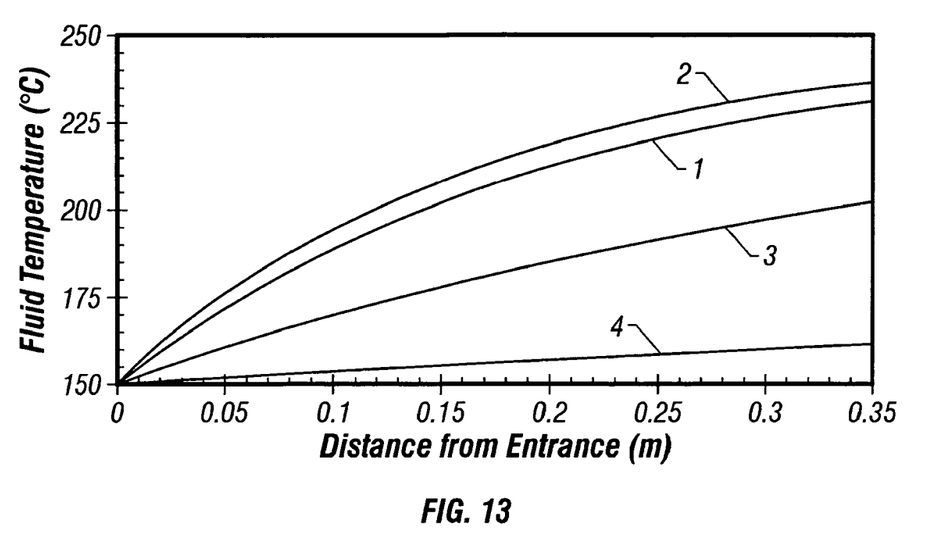
FIG. 13 is a graph showing exemplary results.

FIG. 13 is a graph showing the results determined from Example 3. The results show the calculated fluid temperature as a function of distance from the reactor tube entrance for a void tube, a tube with a packed bed of catalyst rings, and tubes with the exemplary inserts described in Examples 1 and 2. The x-axis represents a distance in meters from the entrance of the reactor tube. The y-axis shows the fluid temperature in degrees Celsius to indicate the heat transfer along the length of the reactor tube.

The lower curve 4 for the void tube has the lowest rate of heat transfer. The temperature increase is about 10° C. through the reactor or about a 7% increase from the starting temperature of about 150° C. The next higher curve 3, using a packed bed, shows the rate of heat transfer of about 50° C. or about a 33% increase. The next higher curve 1, using the insert constructed according to Example 1, shows a greater heat transfer ability by increasing the temperature by about 80° C. or about a 53% increase. The final curve 2, using the insert constructed according to Example 2, shows the largest heat transfer ability by increasing the temperature by about 85° C. or about a 57% increase.

Example 4

Pressure Drop

The same experimental conditions as specified in Example 3 are maintained. The pressure drop, calculated per metre length, is determined for the tube charged with the inserts in Examples 1 and 2 and for the void tube according to Karman-Nikuradze, see J. Nikuradze, VDI-Vorschungsheft (1950) 361. The pressure drop for the tube charged with the ring-formed particles is determined according to S. Ergun, Chem. Eng. Prog., 48, 89, 1952.

The thus determined pressure drops are as follows.
 For the void tube: 5 Pa per metre
 For the ring-formed particles: 18000 Pa per metre
 For the insert in Example 1: 870 Pa per metre
 For the insert in Example 2: 485 Pa per metre.

Example 5

Turbulence

The same experimental conditions as specified in Example 3 are maintained. The turbulence inside the tubular reactor at a superficial fluid velocity of 1 m/s was calculated, expressed in the Reynolds numbers as follows.

For the void tube: 30516,
For the ring-formed particles: 9720,
For insert in Example 1: 10681,
For insert in Example 2: 5148.

From these results it is clear that, under the condition of high fluid velocity used, the inserts decrease rather than increase the turbulence inside the reactor tube. In particular it is shown here that the increased heat transfer, found in Example 3 for the two inserts according to the invention (compared to the ring-formed particles) is not due to an increased turbulence.

We claim:

1. A multi-tubular reactor system for catalytically reacting a fluid reactant mixture to form a fluid product comprising a shell and a plurality of reactor tubes housed therein which reactor tubes comprise:
   a heating zone; and
   a reaction zone positioned downstream from the heating zone,
wherein the reactor tubes contain a heat-exchanging essentially rod-shaped insert having a length of from 1% to 20% of the total length of the reactor tube disposed within the heating zone and a bed of solid particulate catalyst disposed within the reaction zone, and the reactor system is adapted to allow heat-exchange fluid to flow between the shell and the external surface of the reactor tubes.

2. The multi-tubular reactor system as claimed in claim 1, wherein the reactor tubes further comprise a cooling zone positioned downstream from the reaction zone, and the reactor tubes further contain a heat-exchanging essentially rod-shaped insert having a length of from 1% to 20% of the total length of the reactor tube disposed within the cooling zone.

3. The multi-tubular reactor system as claimed in claim 1, wherein the insert has a length of from 1% to 5% of the total length of the reactor tube.

4. The multi-tubular reactor system as claimed in claim 1, wherein the insert has a heat transfer coefficient in the range of from 800 to 4000 $Wm^{-2}K^{-1}$, based on inner tube surface area, and the pressure drop along the tube portion occupied by the insert is in the range of from 0.05 and 20 $kPam^{-1}$ at Reynolds numbers in the range of from 10,000 to 50,000, based on void tube dimensions and superficial velocity.

5. The multi-tubular reactor system as claimed in claim 1, wherein the insert has essentially the form of a cylinder having a core with a cross-sectional external surface area in the range of from 20% to 90% of the cross-sectional internal surface area of the reactor tube.

6. The multi-tubular reactor system as claimed in claim 5, wherein the insert further comprises sufficient surface protrusions in contact with the inside surface of the reactor tube to secure the insert in position inside the reactor tube.

7. The multi-tubular reactor system as claimed in claim 6, wherein the surface protrusions have surface areas and thicknesses that increase towards the outer circumference of the core.

8. The multi-tubular reactor system as claimed in claim 6, wherein the insert comprises a means for adjusting the outer surface such that the surface protrusions are brought into contact with, or closer proximity to, the inner surface of the reactor tube after installation in the reactor tube.

9. The multi-tubular reactor system as claimed in claim 6, wherein the surface protrusions are selected from the group consisting of rings, bars, helices, and combinations thereof.

10. The multi-tubular reactor system as claimed in claim 6, wherein the surface protrusions comprise wire mesh.

11. The multi-tubular reactor system as claimed in claim 6, wherein the surface protrusions comprise brush bristles.

12. The multi-tubular reactor system as claimed in claim 6, wherein the surface protrusions comprise longitudinally positioned smooth plates.

13. The multi-tubular reactor system as claimed in claim 6, wherein the surface protrusions comprise longitudinally positioned corrugated plates.

14. The multi-tubular reactor system as claimed in claim 6, wherein the surface protrusions comprise fins.

15. The multi-tubular reactor system as claimed in claim 6, wherein the surface protrusions comprise wings.

16. The multi-tubular reactor system as claimed in claim 5, wherein the insert comprises a means for adjusting the outer surface of the insert itself, or the core of the insert, such that the insert is brought into contact with the inner surface of the reactor tube after installation in the reactor tube.

17. The multi-tubular reactor system as claimed in claim 1, wherein the insert comprises a metal or an alloy resistance to corrosion under reaction conditions.

18. The multi-tubular reactor system as claimed in claim 1, wherein the insert has the form of a rod-shaped core-less wire mesh which is in contact with the inside surface of the reactor tube.

19. The multi-tubular reactor system as claimed in claim 1, wherein the fluid reactant mixture comprises ethylene and oxygen and the fluid product comprises ethylene oxide.

20. The multi-tubular reactor system as claimed in claim 1, wherein the fluid reactant mixture comprises carbon monoxide and hydrogen and the fluid product comprises a hydrocarbon and/or an oxygenate thereof.

21. A multi-tubular reactor system for catalytically reacting a fluid reactant mixture to form a fluid product comprising a shell and a plurality of reactor tubes housed therein which reactor tubes comprise:
   a reaction zone; and
   a cooling zone positioned downstream from the reaction zone,
wherein the reactor tubes contain a bed of solid particulate catalyst disposed within the reaction zone and a heat-exchanging essentially rod-shaped insert having a length of from 1% to 20% of the total length of the reactor tube disposed within the cooling zone, and the reactor system is adapted to allow heat-exchange fluid to flow between the shell and the external surface of the reactor tubes.

22. The multi-tubular reactor system as claimed in claim 21, wherein the insert has a length of from 1% to 5% of the total length of the reactor tube.

23. The multi-tubular reactor system as claimed in claim 21, wherein the insert has a heat transfer coefficient in the range of from 800 to 4000 $Wm^{-2}K^{-1}$, based on inner tube surface area, and the pressure drop along the tube portion occupied by the insert is in the range of from 0.05 and 20 $kPam^{-1}$ at Reynolds numbers in the range of from 10,000 to 50,000, based on void tube dimensions and superficial velocity.

24. The multi-tubular reactor system as claimed in claim 21, wherein the insert has essentially the form of a cylinder having a core with a cross-sectional external surface area in the range of from 20% to 90% of the cross-sectional internal surface area of the reactor tube.

25. The multi-tubular reactor system as claimed in claim 24, wherein the insert further comprises sufficient surface protrusions in contact with the inside surface of the reactor tube to secure the insert in position inside the reactor tube.

26. The multi-tubular reactor system as claimed in claim 25, wherein the surface protrusions are selected from the group consisting of rings, bars, helices, and combinations thereof.

27. The multi-tubular reactor system as claimed in claim 25, wherein the surface protrusions comprise longitudinally positioned smooth plates.

28. The multi-tubular reactor system as claimed in claim 25, wherein the surface protrusions comprise longitudinally positioned corrugated plates.

29. The multi-tubular reactor system as claimed in claim 21, wherein the insert comprises a metal or an alloy resistance to corrosion under reaction conditions.

30. The multi-tubular reactor system as claimed in claim 21, wherein the insert has the form of a rod-shaped core-less wire mesh which is in contact with the inside surface of the reactor tube.

* * * * *